United States Patent [19]

Walter

[11] Patent Number: 5,071,968
[45] Date of Patent: Dec. 10, 1991

[54] AZO DYES CONTAINING A 7-SULFOALKANOYLAMINO-1,2,3,4-TETRAHYDROQUINOLINE COUPLING COMPONENT

[75] Inventor: Harald Walter, Basel, Switzerland

[73] Assignee: Ciba-Geigy Corporation, Ardsley, N.Y.

[21] Appl. No.: 488,573

[22] Filed: Mar. 5, 1990

[30] Foreign Application Priority Data

Mar. 6, 1989 [CH] Switzerland ............................ 816/89
Jul. 24, 1989 [CH] Switzerland .......................... 2764/89

[51] Int. Cl.$^5$ ..................... C09B 29/44; C09B 29/033; D06P 1/06
[52] U.S. Cl. .................................. 534/768; 534/728; 534/770
[58] Field of Search ................................ 534/768, 770

[56] References Cited

U.S. PATENT DOCUMENTS

| | | | |
|---|---|---|---|
| 4,255,326 | 3/1981 | Giles et al. ............................ | 534/768 |
| 4,265,812 | 5/1981 | Weaver et al. ....................... | 534/768 |
| 4,282,144 | 8/1981 | Weaver et al. ....................... | 534/768 |
| 4,301,068 | 11/1981 | Giles et al. ....................... | 534/768 X |
| 4,301,069 | 11/1981 | Weaver et al. ....................... | 534/736 |
| 4,301,070 | 11/1981 | Giles et al. ....................... | 534/768 X |
| 4,301,071 | 11/1981 | Giles et al. ............................ | 534/752 |
| 4,302,387 | 11/1981 | Giles et al. ............................ | 534/768 |
| 4,302,390 | 11/1981 | Giles et al. ....................... | 534/768 X |
| 4,400,318 | 8/1983 | Weaver et al. ....................... | 534/768 |
| 4,530,997 | 7/1985 | Weaver et al. ....................... | 534/768 |
| 4,554,348 | 11/1985 | Gourley ............................... | 534/768 |
| 4,575,482 | 3/1986 | Lenoir ................................... | 430/431 |

FOREIGN PATENT DOCUMENTS

| | | |
|---|---|---|
| 0040172 | 11/1981 | European Pat. Off. . |
| 3840113 | 6/1989 | Fed. Rep. of Germany ...... 534/768 |
| 1335279 | 10/1973 | United Kingdom . |
| 2147603 | 5/1985 | United Kingdom . |
| 2148917 | 5/1985 | United Kingdom . |
| 2151651 | 7/1985 | United Kingdom ................ 534/768 |
| 2216137 | 10/1989 | United Kingdom ................ 534/768 |

OTHER PUBLICATIONS

Hackh's Chemical Dictionary, 4th Ed. pp. 675 & 677 (1969).

*Primary Examiner*—Mary C. Lee
*Assistant Examiner*—Fiona T. Powers
*Attorney, Agent, or Firm*—George R. Dohmann; Edward McC. Roberts

[57] ABSTRACT

Azo dyes of the formula

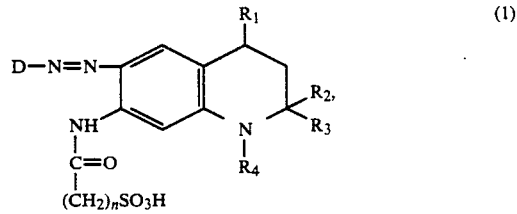

where D is a diazo component, $R_1$, $R_2$, $R_3$ and $R_4$ are each independently of the others hydrogen or substituted or unsubstituted $C_1$–$C_8$alkyl, and n is 1,2,3,4 or 5, produce dyeings of good fastness properties on nitrogen-containing or hydroxyl-containing fibre materials.

17 Claims, No Drawings

AZO DYES CONTAINING A 7-SULFOALKANOYLAMINO-1,2,3,4-TETRAHYDROQUINOLINE COUPLING COMPONENT

The present invention relates to novel azo dyes, to processes for preparing same and to the use thereof for dyeing and printing fibre materials, in particular textile fibre materials.

The present invention accordingly provides azo dyes of the formula

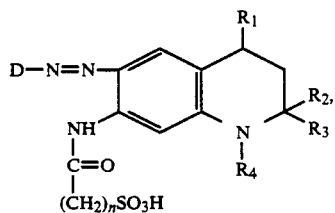

where D is a diazo component, $R_1$, $R_2$, $R_3$ and $R_4$ are each independently of the others hydrogen or substituted or unsubstituted $C_1$-$C_8$alkyl, and n is 1, 2, 3, 4 or 5.

D may contain the customary diazo component substituents, for example alkyl of 1 to 8, preferably 1 to 4 carbon atoms, e.g. methyl, ethyl, propyl, isopropyl, butyl, isobutyl, sec-butyl, tert-butyl, hexyl or octyl, which may each be substituted by sulfo of sulfato, alkoxy of 1 to 8 carbon atoms, in particular 1 to 4 carbon atoms, e.g. methoxy, ethoxy, propoxy, isopropoxy or butoxy, acylamino such as alkanoylamino of 2 to 8 carbon atoms and alkoxycarbonylamino of 2 to 8 carbon atoms, e.g. acetylamino, propionylamino, methoxycarbonylamino or ethoxycarbonylamino, alkanoyl of 2 to 8, preferably 2 to 4, carbon atoms, e.g. acetyl, propionyl, butyryl or isobutyryl, $C_5$-$C_7$cycloalkylcarbonyl, e.g. cyclohexylcarbonyl, $C_5$-$C_7$cycloalkylcarbonyl which is substituted in the cycloalkyl ring by $C_1$-$C_4$alkyl, e.g. methyl, ethyl, propyl or butyl, halogen, e.g. fluorine, chlorine or bromine, sulfo or sulfato, benzoyl, benzoyl which is substituted in the phenyl ring by $C_1$-$C_4$alkyl, e.g. methyl, ethyl, propyl or butyl, halogen, e.g. fluorine, chlorine or bromine, sulfo or sulfato, unsubstituted or sulfo-substituted $C_1$-$C_8$alkylthio, e.g. methylthio, ethylthio or β-sulfoethylthio, unsubstituted or $C_1$-$C_4$alkyl-, halogen-, sulfo- or sulfato-substituted benzothiazole or benzoxazole, benzoylamino, amino, mono- or dialkylamino having 1 to 8 carbon atoms in the alkyl moiety, phenylamino, alkoxycarbonyl having 1 to 8 carbon atoms in the alkoxy moiety, $C_5$-$C_7$cycloalkylaminosulfonyl, nitro, cyano, trifluoromethyl, halogen, such as fluorine, bromine or in particular chlorine, sulfamoyl, sulfamoyl which is monosubstituted or disubstituted on the nitrogen atom by $C_1$-$C_4$alkyl, $C_5$-$C_7$cycloalkyl, phenyl or naphthyl, phenyl- or naphthyl-aminosulfonyl which is substituted in the phenyl or naphthyl ring by $C_1$-$C_4$alkyl, halogen, e.g. fluorine, bromine or in particular chlorine, sulfo or sulfato, carbamoyl, ureido, hydroxyl, $C_1$-$C_8$alkylsulfonyl, $C_1$-$C_8$alkylaminosulfonyl, unsubstituted or $C_1$-$C_4$alkyl-, halogen-, e.g. fluorine-, chlorine-or bromine-, sulfo- or sulfato-substituted (in the phenyl or naphthyl ring) phenylsulfonyl or naphthylsulfonyl, 1-azacycloheptane-N-sulfonyl, carboxyl, sulfomethyl, sulfo, sulfato, thiosulfato, arylazo, e.g. phenylazo or naphthylazo, or phenyl, naphthyl, phenoxy, phenoxysulfonyl or phenylaminosulfonyl, in which the naphthyl and phenyl radicals mentioned may each be further substituted by the abovementioned substituents. Where possible, any two adjacent substituents on the ring systems mentioned may form further fused-on phenyl or cyclohexyl rings.

$C_1$-$C_8$alkyl $R_1$, $R_2$, $R_3$ or $R_4$ in the formula (1) is for example: methyl, ethyl, propyl, isopropyl, butyl, isobutyl, sec-butyl, tert-butyl, pentyl, hexyl, heptyl or octyl, or the corresponding radicals which are substituted for example by hydroxyl, alkoxy of 1 to 4 carbon atoms, e.g. methoxy, ethoxy, propoxy, isopropoxy or butoxy, sulfo, sulfato, thiosulfato, cyano or halogen, e.g. fluorine, chlorine or bromine, or phenyl, which phenyl may be further substituted by the abovementioned substituents.

Preference is given to azo dyes of the formula (1) where $R_1$ is hydrogen or $C_1$-$C_4$alkyl, in particular methyl.

Preference is further given to azo dyes of the formula (1) where $R_2$ and $R_3$ are each independently of the other hydrogen or $C_1$-$C_4$alkyl, in particular methyl.

Preference is also given to azo dyes of the formula (1) where $R_4$ is $C_1$-$C_4$alkyl, in particular ethyl, or benzyl.

Preference is further given to azo dyes of the formula (1), where n is 1, 2 or 3, in particular 1 or 2.

The azo dyes of the formula (1) preferably contain only one or two sulfo, sulfato or thiosulfato groups, in particular two sulfo groups.

Preference is likewise given to azo dyes of the formula

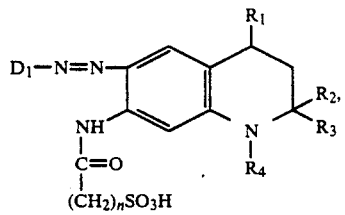

where $D_1$ is the radical of a diazo component of the benzene or naphthalene series or of the heterocyclic series, in particular thienyl, thiazolyl, isothiazolyl, 1,2,4-thiadiazolyl, 1,3,4-thiadiazolyl, benzothiazolyl, benzisothiazolyl, benzoxazolyl, pyrazolyl, imidazolyl, 1,2,3-triazolyl, 1,2,4-triazolyl, thiophenyl, benzothiophenyl, tetrahydrobenzothiophenyl, 7-oxotetrahydrobenzo[b]thiophenyl, pyridinyl, indazolyl, phenyl or naphthyl, each of which may be substituted by $C_1$-$C_8$alkyl, $C_1$-$C_8$alkoxy, $C_2$-$C_8$alkanoylamino, $C_2$-$C_8$alkoxycarbonylamino, $C_2$-$C_8$alkanoyl, $C_5$-$C_7$cycloalkylcarbonyl, $C_5$-$C_7$cycloalkylcarbonyl which is substituted in the cycloalkyl ring by $C_1$-$C_4$alkyl, halogen, sulfo or sulfato, benzoyl, benzoyl which is substituted in the phenyl ring by $C_1$-$C_4$alkyl, halogen, sulfo or sulfato, $C_1$-$C_8$alkylthio, sulfo-substituted $C_1$-$C_8$alkylthio, benzothiazole, benzoxazole, $C_1$-$C_4$alkyl-, halogen-, sulfo- or sulfato-substituted benzothiazole or benzoxazole, benzoylamino, amino, mono- or dialkylamino having 1 to 8 carbon atoms in the alkyl moiety, phenylamino, $C_2$-$C_8$alkoxycarbonyl, nitro, cyano, trifluoromethyl, halogen, 1-azacycloheptane-N-sulfonyl, sulfamoyl, sulfamoyl which is monosubstituted or disubstituted on the nitrogen atom by $C_1$-$C_4$alkyl, $C_5$-$C_7$cycloalkyl, phenyl or naphthyl, phenyl- or naphthyl-aminosulfonyl which is substituted in the phenyl or naphthyl ring by $C_1$-$C_4$alkyl, halogen, sulfo or sulfato, phenoxy, phenoxysulfonyl, $C_1$-$C_4$alkyl-, halogen-, sulfo- or sulfato-substituted phenoxy or phenoxysulfonyl, carbamoyl, ureido, hydroxyl, $C_1$-$C_8$alkylsulfonyl, phenylsulfonyl, naphthylsulfonyl, phenyl- or naphthyl-sulfonyl which is substituted in the phenyl or naphthyl ring by $C_1$-$C_4$alkyl, halogen, sulfo or sulfato, carboxyl, sulfomethyl, sulfo, sulfato, thiosulfato, phenylazo or naphthylazo, and where possible any 2 adjacent substitutents on the ring systems mentioned may form further fused-on phenyl or cyclohexyl rings, and $R_1$, $R_2$, $R_3$, $R_4$ and n are each as defined under formula (1), preferably where each of the radicals mentioned above for $D_1$ may be substituted by $C_1$-$C_8$alkyl, $C_1$-$C_8$alkoxy, $C_2$-$C_8$alkanoylamino, $C_2$-$C_8$alkoxycarbonylamino, $C_2$-$C_8$alkanoyl, $C_5$-$C_7$cycloalkylcarbonyl, $C_5$-$C_7$cycloalkylcarbonyl which is substituted in the cycloalkyl ring by $C_1$-$C_4$alkyl, halogen, sulfo or sulfato, benzoyl, benzoyl which is substituted in the phenyl ring by $C_1$-$C_4$alkyl, halogen, sulfo or sulfato, benzothiazole, benzoxazole, $C_1$-$C_4$alkyl-, halogen-, sulfo- or sulfato-substituted benzothiazole or benzoxazole, benzoylamino, amino, mono- and dialkylamino having 1 to 8 carbon atoms in the alkyl moiety, phenylamino, $C_2$-$C_8$alkoxycarbonyl, nitro, cyano, trifluoromethyl, halogen, sulfamoyl, sulfamoyl which is monosubstituted or disubstituted on the nitrogen atom by $C_1$-$C_4$alkyl, $C_5$-$C_7$cycloalkyl or phenyl, carbamoyl, ureido, hydroxyl, $C_1$-$C_8$alkylsulfonyl, phenylsulfonyl, phenylsulfonyl which is substituted in the phenyl ring by $C_1$-$C_4$alkyl, halogen, sulfo or sulfato, carboxyl, sulfomethyl, sulfo, sulfato, thiosulfato, phenylazo or naphthylazo, and where possible any 2 adjacent substituents on the ring systems mentioned may form further fused-on phenyl or cyclohexyl rings and $R_1$, $R_2$, $R_3$, $R_4$ and n are each as defined under the formula (1).

Particular preference is given to azo dyes of the formula

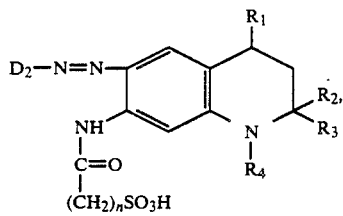

(3)

where $D_2$ is thiophenyl, benzothiophenyl, benzisothiazolyl, 1,3,4-thiadiazolyl, 7-oxotetrahydrobenzo[b]thiophenyl or phenyl, each of which may be substituted by $C_1$-$C_8$alkyl, $C_1$-$C_8$alkoxy, $C_2$-$C_8$alkanoyl, carbamoyl, $C_2$-$C_8$alkoxycarbonyl, $C_5$-$C_7$cycloalkylcarbonyl, benzoyl, benzoyl which is substituted in the phenyl ring by $C_1$-$C_4$alkyl, halogen, sulfo or sulfato, $C_1$-$C_8$alkylthio, sulfo-substituted $C_1$-$C_8$alkylthio, benzothiazole, benzoxazole, $C_1$-$C_4$alkyl-, halogen-, sulfo- or sulfato-substituted benzothiazole or benzoxazole, halogen, sulfo, trifluoromethyl, phenylsulfonyl, naphthylsulfonyl, phenyl- or naphthyl-sulfonyl which is substituted in the phenyl or naphthyl ring by $C_1$-$C_4$alkyl, halogen, sulfo or sulfato, $C_1$-$C_8$alkylsulfonyl, 1-azacycloheptane-N-sulfonyl, sulfamoyl, sulfamoyl which is monosubstituted or disubstituted on the nitrogen atom by $C_1$-$C_4$alkyl, $C_5$-$C_7$cycloalkyl, phenyl or naphthyl, phenyl- or naphthyl-aminosulfonyl which is substituted in the phenyl or naphthyl ring by $C_1$-$C_4$alkyl, halogen, sulfo or sulfato, phenoxy, phenoxysulfonyl, $C_1$-$C_4$alkyl-, halogen-, sulfo- or sulfato-substituted phenoxy or phenoxysulfonyl, and $R_1$, $R_2$, $R_3$, $R_4$ and n are each as defined under the formula (1), preferably where each one of the radicals mentioned above for $D_2$ may be substituted by $C_1$-$C_8$alkyl, $C_2$-$C_8$alkanoyl, $C_2$-$C_8$alkoxycarbonyl, $C_5$-$C_7$cycloalkylcarbonyl, benzoyl, benzoyl which is substituted in the phenyl ring by $C_1$-$C_4$alkyl, halogen, sulfo or sulfato, benzothiazole, benzoxazole, $C_1$-$C_4$alkyl-, halogen-, sulfo- or sulfato-substituted benzothiazole or benzoxazole, halogen, phenylsulfonyl, phenylsulfonyl which is substituted in the phenyl ring by $C_1$-$C_4$alkyl, halogen, sulfo or sulfato, $C_1$-$C_8$alkylsulfonyl, sulfamoyl which is monosubstituted or disubstituted on the nitrogen atom by $C_1$-$C_4$alkyl, $C_5$-$C_7$cycloalkyl or phenyl, and $R_1$, $R_2$, $R_3$, $R_4$ and n are each as defined under the formula (1).

Particular preference is given to azo dyes of the formula (1) where $R_1$ is hydrogen or $C_1$-$C_4$alkyl, in particular methyl, $R_2$ and $R_3$ are each independently of the other hydrogen or $C_1$-$C_4$alkyl, in particular methyl, $R_4$ is $C_1$-$C_4$alkyl, in particular ethyl, n is 1 or 2, and D is as defined under the formula (1), in particular where D has the meanings defined for $D_1$ under the formula (2), preferably the meanings defined for $D_2$ under the formula (3).

Also of interest are azo dyes of the formula (2) where $R_1$ is hydrogen or methyl, $R_2$ and $R_3$ are each independently of the other hydrogen or methyl, $R_4$ is ethyl, n is 1 or 2, and $D_1$ is as defined under formula (2) and has in particular the meanings defined for $D_2$ under the formula (3).

Very particular preference is given to azo dyes of the formula

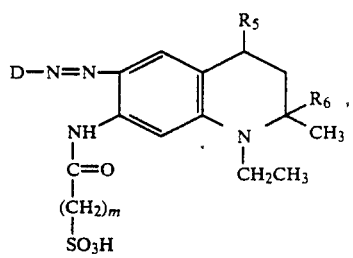

(4)

where $R_5$ and $R_6$ are each independently of the other hydrogen or methyl, m is 1 or 2, and D is as defined under formula (1) and has in particular the meanings defined for $D_1$ under the formula (2).

Preferably, D in the formula (4) has the meanings defined for $D_2$ under the formula (3).

Of particular interest are azo dyes of the formula (4) where $R_5$ and $R_6$ are both hydrogen or methyl.

Of very particular importance are azo dyes of the formula (4) where $R_5$ and $R_6$ are both hydrogen or methyl, m is 1 or 2, and D has the meanings defined for $D_1$ under formula (2), in particular the meanings defined for $D_2$ under the formula (3).

The present invention also provides a process for preparing the azo dyes of the formula (1), which comprises diazotizing an amine of the formula

D—NH$_2$   (5)

and coupling it onto a coupling component of the formula

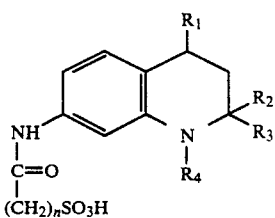

(6)

where D, $R_1$, $R_2$, $R_3$, $R_4$ and n are each as defined under the formula (1).

If desired, the coupling may be followed by introduction into the azo dye of the formula (1) of a further water-solubilizing group; furthermore, the coupling may also be followed by alkylation or acylation.

The diazo component of the formula (5) is in general diazotized by the action of nitrous acid at a low temperature in an aqueous solution of a mineral acid and coupled onto the coupling component of formula (6) at acid or neutral pH.

If desired, a free amino group in the radical D can be converted, after coupling, into an acylamino or alkylamino group by acylation or alkylation; similarly, an hydroxyl group can be converted into an acyloxy or alkoxy group by acylation or alkylation.

Furthermore, a free hydroxyl group may be converted into a water-solubilizing group, for example into a sulfato group by sulfation.

Preferably, the process according to the present invention is carried out with amines of the formula (5) where D has the meanings defined for $D_1$ under the formula (2) or in particular the meanings defined for $D_2$ under the formula (3).

The process according to the present invention is preferably carried out with coupling components of the formula (6) where $R_1$ is hydrogen or $C_1$-$C_4$alkyl, in particular methyl.

The process according to the present invention is preferably further carried out with coupling components of the formula (6) where $R_2$ and $R_3$ are each independently of the other hydrogen or $C_1$-$C_4$alkyl, in particular methyl.

The process according to the present invention is preferably further carried out with coupling components of the formula (6) where $R_4$ is $C_1$-$C_4$alkyl in particular ethyl, or benzyl.

The process according to the present invention is preferably further carried out with coupling components of the formula (6) where n is 1, 2 or 3, in particular 1 or 2.

A preferred embodiment of the process for preparing the azo dyes of the formula (1) according to the present invention comprises diazotizing an amine of the formula (5) where D is as defined under the formula (1) but has in particular the meanings defined for $D_1$ under the formula (2) and coupling it onto a coupling component of the formula (6) where $R_1$ is hydrogen or $C_1$-$C_4$alkyl, in particular methyl, $R_2$ and $R_3$ are each independently of the other hydrogen or $C_1$-$C_4$alkyl, in particular methyl, $R_4$ is $C_1$-$C_4$alkyl, in particular ethyl, and n is 1 or 2. Preference is given to using an amine of the formula (5) where D has the meanings defined for $D_2$ under the formula (3).

The very particularly preferred azo dyes of the formula (4) are prepared by diazotizing an amine of the formula (5) where D is as defined under the formula (1) but has in particular the meanings defined for $D_1$ under the formula (2) and coupling it onto a coupling component of the formula

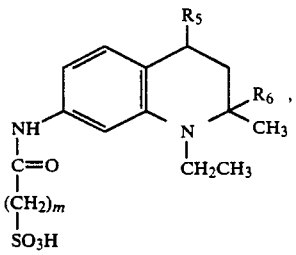

(7)

where $R_5$ and $R_6$ are each independently of one another hydrogen or methyl and m is 1 or 2. The process for preparing the azo dyes of the formula (4) according to the present invention is preferably carried out with an amine of the formula (5) where D has the meanings defined for $D_2$ under the formula (3).

A preferred embodiment of the process for preparing the azo dyes of the formula (4) according to the present invention comprises using a coupling component of the formula (7) where $R_5$ and $R_6$ are both hydrogen or methyl.

A particularly preferred embodiment of the process for preparing the azo dyes of the formula (4) according to the present invention comprises using a coupling component of the formula (7) where $R_5$ and $R_6$ are both hydrogen or methyl and m is 1 or 2.

Of the large number of possible amines of the formula (5) it is possible to use for example:

2-amino-3-methoxycarbonylthiophene,
2-amino-3-ethoxycarbonylthiophene,
2-amino-3-methoxycarbonyl-5-isobutyrylthiophene,
2-amino-3,5-dimethoxycarbonylthiophene,
2-amino-3,5-dimethoxycarbonyl-4-methylthiophene,
2-amino-3,5-diethoxycarbonyl-4-methylthiophene,
2-amino-3-methoxycarbonyl-5-(p-methylbenzoyl)thiophene,
2-amino-3-methoxycarbonyl-5-cyclohexylcarbonylthiophene,
2-amino-3-ethoxycarbonyl-5-(benzothiazol-2'-yl)thiophene,
2-amino-3-methoxycarbonyl-5-(benzothiazol-2'-yl)thiophene,
2-amino-3-ethoxycarbonyl-5-(benzoxazol-2'-yl)thiophene,
2-amino-3-methoxycarbonyl-5-(benzoxazol-2'-yl)thiophene,
2-amino-3-methoxycarbonyl-4-methyl-5-(benzothiazol-2'-yl)thiophene,
2-amino-3-ethoxycarbonyl-4-methyl-5-(benzothiazol-2'-yl)thiophene,
2-amino-3-methoxycarbonyl-4-methyl-5-(benzoxazol-2'-yl)thiophene,
2-amino-3-ethoxycarbonyl-4-methyl-5-(benzoxazol-2'-yl)thiophene,
2-chloro-4-methylsulfonylaniline,4-methylsulfonylaniline,
2-chloro-4-ethylsulfonylaniline,
4-ethylsulfonylaniline,
2-phenylsulfonylaniline,
4-phenylsulfonylaniline,
2-(p-chlorophenyl)sulfonyl-5-ethylsulfonylaniline,
2-(1-azacycloheptane-N-sulfonyl)aniline, 7-oxotetrahydrobenzo[b]-2-amino-3-methoxycarbonyl-6-methylthiophene,
7-oxotetrahydrobenzo[b]-2-amino-3-methoxycarbonylthiophene,
7-oxotetrahydrobenzo[b]-2-amino-3-ethoxycarbonyl-6-methylthiophene,
7-oxotetrahydrobenzo[b]-2-amino-3-ethoxycarbonylthiophene,
2-amino-3-methoxycarbonyl-5-(5'- or 6'-sulfobenzothiazol-2'-yl)thiophene,
2-amino-3-ethoxycarbonyl-5-(5'- or 6'-sulfobenzothiazol-2'-yl)thiophene,
2-amino-3-carbamoyl-5-(5'- or 6'-sulfobenzothiazol-2'-yl)thiophene,
2-amino-3-carbamoyl-5-(benzothiazol-2'-yl)thiophene,
2-amino-3-methoxycarbonyl-5-(5'- or 6'-sulfobenzoxazol-2'-yl)thiophene,
2-amino-3-ethoxycarbonyl-5-(5'- or 6'-sulfobenzoxazol-2'-yl)thiophene,
2-amino-3-carbamoyl-5-(5'- or 6'-sulfobenzoxazol-2'-yl)thiophene,
2-amino-3-carbamoyl-5-(benzoxazol-2'-yl)thiophene,
2-methoxycarbonyl-3-aminobenzothiophene,
2-methoxycarbonyl-3-amino-4-chlorobenzothiophene,
2-methoxycarbonyl-3-aminobenzothiophene-4-, -5-, -6- or -7-sulfonic acid,
2-amino-5-ethylthio-1,3,4-thiadiazole,
2-amino-5-(β-sulfoethylthio)1,3,4-thiadiazole,
3-aminobenzisothiazole,
3-aminobenzisothiazole-7-sulfonic acid,
3-amino-4-, -5-, -6- or -7-chlorobenzisothiazole,
2-(2'-chlorophenylsulfonyl)aniline,
3-phenylaminosulfonyl-4-methylaniline,
4-sulfoamoylaniline,
2-(2'-chlorophenoxy)-5-chloroaniline,
2-trifluoromethyl-4-chloroaniline,
2-trifluoromethylaniline,
2,5-dimethoxy-4-phenylaminosulfonylaniline,
2-methylsulfonylaniline,
2-(2'-amino-4'-sulfamoylphenylsulfonyl)-naphthalene-5-, -6-, -7- or -8-sulfonic acid,
2-amino-4'-methyl-4-(1''-sulfonaphth-2''-ylaminosulfonyl)-1,1'-diphenyl sulfone,
2-amino-4'-methyl-4-(3''-sulfophenylaminosulfonyl)-1,1'-diphenyl sulfone,
2-amino-4-sulfamoyl-3'-sulfo-4'-methyl-1,1'-diphenyl sulfone,
2-amino-3'-sulfo-4'-methyl-4-dimethylaminosulfonyl-1,1'-diphenyl sulfone,
2-amino-4-sulfo-4'-methyl-1,1'-diphenyl sulfone,
2-amino-4'-methyl-4-(4''-sulfophenoxysulfonyl)-1,1'-diphenyl sulfone.

The amines of the formula (5) are known per se and can be prepared similarly to known compounds.

The amines of the formula (5) may contain radicals, for example acetylamino or nitro, which are convertible into amino groups. For example, acetylamino is so convertible by hydrolysis and nitro by reduction.

Furthermore, following diazotization and coupling, a water-solubilizing group may be introduced into the azo dyes, for example by sulfating a hydroxyl group in the amine of the formula (5) and/or in the coupling component of the formula (6).

The compounds of formula (6) where $R_1$, $R_2$, $R_3$, $R_4$ and n are each as defined under the formula (1) are novel and form a further part of the subject-matter of the present invention.

Preference is given to compounds of the formula (6) where $R_1$ is hydrogen or $C_1$-$C_4$alkyl, in particular methyl.

Preference is further given to compounds of the formula (6) where $R_2$ and $R_3$ are each independently of the other hydrogen or $C_1$-$C_4$alkyl, in particular methyl. Preference is also given to compounds of the formula (6) where $R_4$ is $C_1$-$C_4$alkyl, in particular ethyl, or benzyl.

Preference is similarly given to compounds of the formula (6) where n is 1,2 or 3, in particular 1 or 2.

Particular preference is given to compounds of the formula (6) where $R_1$ is hydrogen or $C_1$-$C_4$alkyl, in particular methyl, $R_2$ and $R_3$ are each independently of the other hydrogen or $C_1$-$C_4$alkyl, in particular methyl, $R_4$ is $C_1$-$C_4$alkyl, in particular ethyl, and n is 1 or 2.

Very particular preference is given to compounds of the formula (7) where $R_5$, $R_6$ and m are each as defined under the formula (7).

Of very particular importance are compounds of the formula (7) where $R_5$ and $R_6$ are both hydrogen or methyl and m is 1 or 2.

The present invention further provides a process for preparing the compounds of formula (6), which comprises reacting a compound of the formula

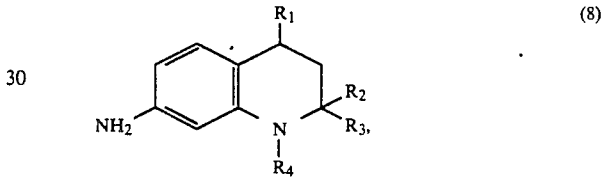

where $R_1$, $R_2$, $R_3$ and $R_4$ are each as defined under formula (1), with a compound of the formula

where X and Y are each an anionic leaving group and n is as defined under formula (1), to give a compound of the formula

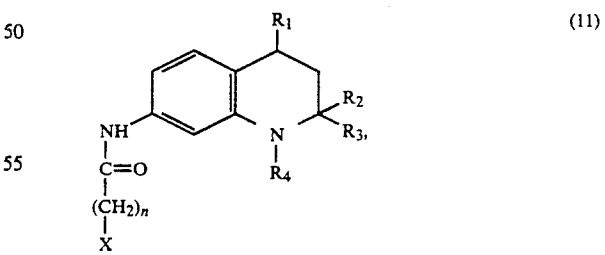

where $R_1$, $R_2$, $R_3$, $R_4$ and n are each as defined under formula (1) and X is as defined under formula (9), and converting the compound of the formula (11) into a compound of the formula (6) by replacing X by sulfo.

X and Y in the formula (9) and X in the formula (10) are each independently of the others for example halogen, e.g. fluorine, chlorine or bromine. In particular, X and Y are both chlorine. Examples of compounds of the formula (9) are chloroacetyl chloride, 3-chloropropionyl chloride, 4-chlorobutyryl chloride and 5-valeryl chloride. Examples of compounds of the formula (10) are the corresponding anhydrides, e.g. chloroacetic anhydride.

The reaction between the compound of the formula (8) and the compound of the formula (9) or (10) is carried out in water or an organic solvent, for example tetrahydrofuran, dioxane or benzene, at temperatures of −10° to 80° C., in particular at temperatures of 0° to 40° C.

The sulfo group is introduced into the compound of the formula (11) by replacing X using for example $Na_2SO_3$ in a solvent, for example water or a water/ethanol mixture, at temperatures of 60° to 130° C., in particular temperatures of 85° to 100° C., at acid, neutral or alkaline pH, in particular at pH 5–9, under atmospheric or superatmospheric pressure, for example under a pressure of 1 to 5 bar.

A preferred embodiment of the process for preparing the compounds of the formula (6) according to the present invention comprises reacting a compound of formula (8) where $R_1$ is hydrogen or $C_1$–$C_4$alkyl, in particular methyl, $R_2$ and $R_3$ are each independently of the other hydrogen or $C_1$–$C_4$alkyl, in particular methyl, and $R_4$ is benzyl or $C_1$–$C_4$alkyl, in particular ethyl, with a compound of the formula (9) where X and Y are both chlorine and n is 1, 2 or 3, in particular 1 or 2, to give a compound of formula (11) where $R_1$, $R_2$, $R_3$ and $R_4$ on the one hand and X and n on the other are each as just defined for the formulae (8) and (9) respectively of this preferred embodiment, and converting the compound of formula (11) by sulfonation, in particular with $Na_2SO_3$, into a compound of the formula (6).

A very particularly preferred embodiment of the process for preparing the compounds of formula (6) according to the present invention comprises using compounds of the formula (8) where $R_1$ and $R_2$ are each independently of the other hydrogen or methyl, $R_3$ is methyl and $R_4$ is ethyl, preferably compounds of the formula (8) where $R_1$ and $R_2$ are both hydrogen or methyl, $R_3$ is methyl and $R_4$ is ethyl.

The dyes of formula (1) are present either in the form of their free acids or preferably as salts thereof.

Suitable salts are for example the alkali metal or ammonium salts and the salts of an organic amine.

Examples of suitable salts are the sodium, lithium, potassium and ammonium salts and the salt of mono-, di- or triethanolamine.

The azo dyes of the formula (1) according to the present invention are suitable for application by dyeing and printing methods known per se, in particular to nitrogen-containing or hydroxyl-containing fibre materials, for example textile fibre materials made of cellulose, silk and in particular wool and synthetic polyamides. Level dyeings are obtained in red and blue shades having good all round fastness properties, in particular good rub, wet, wet rub and light fastness. Furthermore, the dyes according to the present invention are very highly compatible with other dyes. The abovementioned textile materials can be present in a wide variety of processed forms, for example as fibre, yarn, woven fabric or knitted fabric.

In the examples which follow, parts are by weight and the temperatures are in degrees Celsius. Parts by weight bear the same relation to parts by volume as the gram to the cubic centimeter.

EXAMPLE 1

91.4 parts of 7-amino-1-ethyl-1,2,3,4-tetrahydro-2,2,4-trimethylquinoline are dissolved in 285 parts of tetrahydrofuran at room temperature, and 106.6 parts of anhydrous sodium acetate are added with stirring in the course of 2 minutes.

64.2 parts of chloroacetyl chloride are then added dropwise with ice-cooling at an internal temperature of 20° in the course of 30 minutes. The mixture is stirred at 20° for 1 hour, and 250 parts of water are then added dropwise. The mixture is subsequently stirred at 20° for 10 minutes, the aqueous phase is then separated off, and the organic phase is extracted once with 100 parts of 15% aqueous sodium chloride solution. The organic phase is then dried over sodium sulfate, and the crude product is isolated by concentrating the solution in a rotary evaporator. 133.1 parts are obtained of a grey powder of the formula

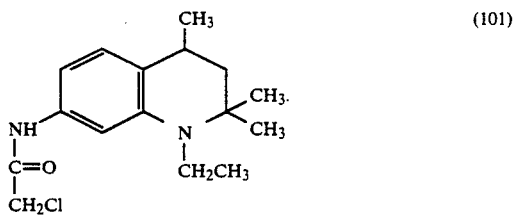

(101)

EXAMPLE 2

Example 1 is repeated, except that the 91.4 parts of 7-amino-1-ethyl-1,2,3,4-tetrahydro-2,2,4-trimethylquinoline are replaced by an equimolar amount of 7-amino-1-ethyl-1,2,3,4-tetrahydro-2-methylquinoline, affording a compound of the formula

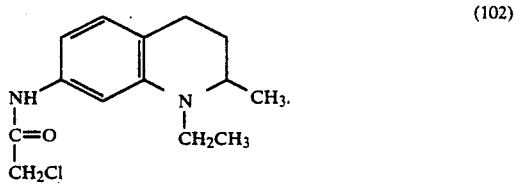

(102)

EXAMPLE 3

58.9 parts of 7-amino-1-ethyl-1,2,3,4-tetrahydro-2,2,4-trimethylquinoline are dissolved in 142 parts of tetrahydrofuran at room temperature. 53 parts of anhydrous sodium acetate are then added, the mixture is cooled down to 0°, and 36 parts of chloropropionyl chloride are added dropwise at an internal temperature of 0° to 3° in the course of 30 minutes. The mixture is subsequently stirred at 0° to 5° for 1 hour, and 125 parts of water are then added dropwise. The mixture is subsequently stirred at 5° for 10 minutes, and the aqueous phase is then separated off in a separating funnel. The organic phase is washed once with 50 parts of water and then dried over sodium sulfate, and the crude product is isolated by concentrating the solution in a rotary evaporator. 74.4 parts are obtained of a grey powder of the formula

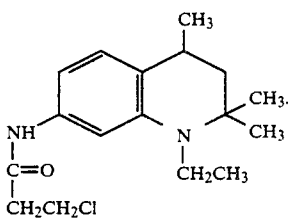

(103)

EXAMPLE 4

Example 3 is repeated, except that the 58.9 parts of 7-amino-1-ethyl-1,2,3,4-tetrahydro-2,2,4-trimethylquinoline are replaced by an equimolar amount of 7-amino-1-ethyl-1,2,3,4-tetrahydro-2-methylquinoline, affording a compound of the formula

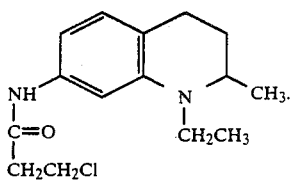

(104)

EXAMPLE 5

133.1 parts of the compound of the formula (101) prepared as described in Example 1 are introduced with stirring into 600 parts of water at room temperature. The pH is then adjusted to 7 by adding 30% aqueous sodium hydroxide solution, and 65 parts of sodium sulfite are added. The temperature is then raised to about 95°, and the mixture is stirred at 93° to 95° for 4 hours. It is then cooled down to 70°, and 105 parts of sodium chloride are sprinkled in over 3 minutes. The mixture is subsequently stirred for 1 hour without heating, cooled down to 15° and filtered. The filter residue is dried at 60° in vacuo for 12 hours and then stirred into 275 parts of absolute ethyl acetate. After 15 minutes' stirring, the product is filtered off with suction, washed with 50 parts of absolute ethyl acetate and dried in air.

This gives 186 parts of a grey powder of the formula

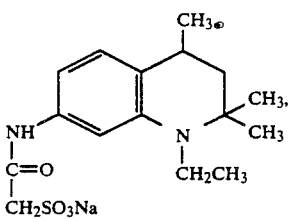

(105)

in a yield of about 75% of theory.

EXAMPLE 6

Example 5 is repeated, except that the 133.1 parts of the compound of the formula (101) are replaced by an equimolar amount of the compound of the formula (102), affording a compound of the formula

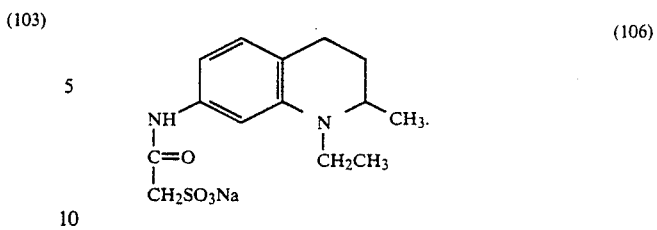

(106)

EXAMPLE 7

74.4 parts of the compound of the formula (103) prepared as described in Example 3 are introduced into 300 parts of water at room temperature, and the pH is adjusted to 7.5 by adding 30% aqueous sodium hydroxide solution. 38 parts of sodium sulfite are then added, and the temperature is raised to 97°. The mixture is heated at 97° for 12 hours while the pH is maintained at a value between 6.8 and 7.0 by the addition of 30% aqueous sodium hydroxide solution. After 12 hours 60 parts of ethanol are added, and the mixture is subsequently stirred at 86° to 88° for a further 12 hours. It is then cooled down to 70° and 200 parts of water are added, followed by 80 parts of sodium chloride added in the course of 2 minutes. The mixture is subsequently stirred for 1 hour without heating, cooled down to 15° and filtered. Drying the filter residue in vacuo leaves 92 parts of a crude product of the formula

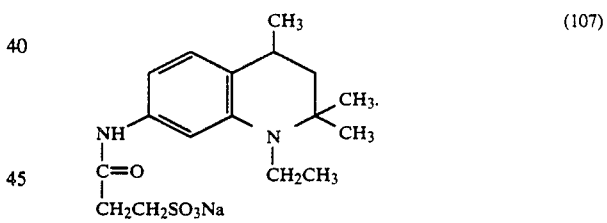

(107)

The crude product can be purified by recrystallization from acetone.

EXAMPLE 8

Example 7 is repeated, except that the 74.4 parts of the compound of the formula (103) are replaced by an equimolar amount of the compound of the formula (104), affording a compound of the formula

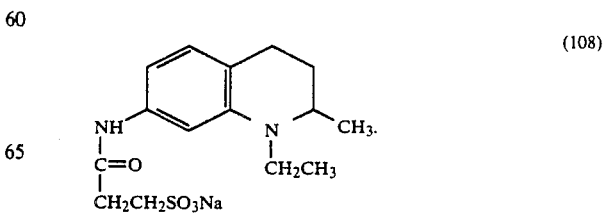

(108)

EXAMPLE 9

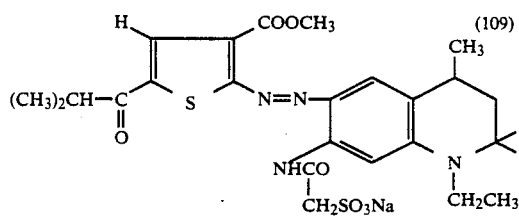

25 parts of glacial acetic acid and 12 parts of 32% hydrochloric acid are introduced as the initial charge at 10° with stirring. 2.3 parts of 2-amino-3-carbomethoxy-5-isobutyrylthiophene are then added, and the temperature is reduced to 0°. A solution of 0.74 part of NaNO$_2$ and 4 parts of water is then added dropwise at 0° to 2° in the course of 3 minutes, and stirred in for 15 minutes, at 0° to 2°. 1 part of sulfamic acid is added, the mixture is briefly stirred, and 3.65 parts of the coupling component of the formula (105) are then added in the course of 1 minute. The mixture is subsequently stirred at 0° to 2° for 5 minutes, and 24 parts of sodium acetate × 3H$_2$O are then added in 4 portions over the next 20 minutes. The mixture is then stirred at 0° for a further 30 minutes, and thereafter admixed with a solution of 6 parts of sodium acetate, 3 parts of sodium carbonate and 30 parts of water added dropwise at an internal temperature of 0° to 3° in the course of 20 minutes. After filtration at room temperature the dye is dried at 50° in vacuo. 6.7 parts are obtained of a black powder of the compound of the formula (109) which dyes natural and synthetic polyamide fibre materials in blue shades.

EXAMPLE 10 TO 30

Example 9 is repeated, except that the 2,3 parts of 2-amino-3-carbomethoxy-5-isobutyrylthiophene are replaced by an equimolar amount of the amines indicated in column 2 of Table 1 and the 3.65 parts of the coupling component of the formula (105) are or are not replaced by an equimolar amount of a coupling component of formula (107). This produces the azo dyes indicated in the form of the free acids in column 3 which dye natural and synthetic polyamide fibre material in the hues indicated in column 4.

TABLE 1

| Ex. | Amine | Azo dye | Hue on nylon and wool |
|---|---|---|---|
| 10 | (structure) | (110) | Blue |
| 11 | (structure) | (111) | Blue |
| 12 | (structure) | (112) | Blue |
| 13 | (structure) | (113) | Blue |

TABLE 1-continued

| Ex. | Amine | Azo dye | Hue on nylon and wool |
|---|---|---|---|
| 14 | H₃C, COOCH₃ on thiophene with H₃COOC and NH₂ | (114) Azo dye with thiophene (H₃C, COOCH₃, H₃COOC) linked N=N to tetrahydroquinoline bearing CH₃, CH₃, CH₃, N-CH₂CH₃, NH-C(=O)-CH₂SO₃H | Violet |
| 15 | H₃C, COOCH₂CH₃ on thiophene with H₃CH₂COOC and NH₂ | (115) corresponding azo dye with NH-C(=O)-CH₂SO₃H | Violet |
| 16 | (CH₃)₂HC-C(=O)- thiophene -COOCH₃, NH₂ | (116) azo dye, NH-C(=O)-CH₂CH₂SO₃H | Blue |
| 17 | cyclohexyl-C(=O)- thiophene -COOCH₃, NH₂ | (117) azo dye, NH-C(=O)-CH₂CH₂SO₃H | Blue |
| 18 | CH₃-C₆H₄-C(=O)- thiophene -COOCH₃, NH₂ | (118) azo dye, NH-C(=O)-CH₂CH₂SO₃H | Blue |
| 19 | fused cyclohexanone-thiophene -COOCH₃, NH₂ | (119) azo dye, NH-C(=O)-CH₂CH₂SO₃H | Blue |

TABLE 1-continued

| Ex. | Amine | Azo dye | Hue on nylon and wool |
|---|---|---|---|
| 20 | | (120) | Blue |
| 21 | | (121) | Red |
| 22 | | (122) | Red |
| 23 | | (123) | Red |
| 24 | | (124) | Red |
| 25 | | (125) | Yellowish red |
| 26 | | (126) | Violet |

TABLE 1-continued

| Ex. | Amine | Azo dye | Hue on nylon and wool |
|---|---|---|---|
| 27 | HO₃SCH₂CH₂S—C(=N—N(H))—S—C(NH₂) | (127) HO₃SCH₂CH₂S—C(=N—N)—S—C(N=N—Ar) where Ar = 2-(NHC(=O)CH₂SO₃H)-4-(CH(CH₃)CH₂C(CH₃)₂N(CH₂CH₃))-phenyl | Strongly bluish red |
| 28 | 2-aminobenzisothiazole | (128) corresponding azo dye with same coupler | Blue |
| 29 | 2-amino-benzisothiazole-SO₃H | (129) corresponding azo dye | Blue |
| 30 | 5-chloro-2-aminobenzisothiazole | (130) corresponding azo dye | Blue |

EXAMPLE 31

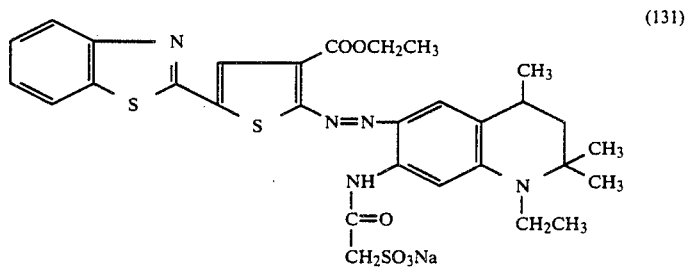

(131)

22.5 parts of 100% acetic acid, 33 parts of 80% acetic acid and 12 parts of 32% hydrochloric acid are introduced as the initial charge at about 10° with stirring. 3.2 parts of 2-amino-5-(benzothiazol-2'-yl)-3-carbethoxythiophene are then added portionwise in the course of 2 50 minutes, and the temperature is reduced to 0°. A solution of 0.74 part of NaNO₂ in 3 parts of water is then added, and diazotization is carried out at 0° to 2° and the diazotization mixture is subsequently stirred at 0° for 20 minutes. It is briefly stirred again after the addition of 1 part of sulfamic acid. 3.65 parts of the coupling component of the formula (105) are then added at 0° in the course of 1 minute. The mixture is subsequently stirred at 0° to 2° for 10 minutes, and 24 parts of sodium acetate×3H$_2$O are then added in 4 portions over the next 20 minutes. After 30 minutes' stirring at 0° to 2° a solution of 6 parts of sodium acetate, 3 parts of sodium carbonate and 30 parts of water is added dropwise at 0° to 3° in the course of 30 minutes, the ice-bath is removed, and 125 parts of 15% aqueous sodium chloride solution are added to the reaction mixture. After filtration, the dye obtained is dried at 50° in vacuo. 8.9 parts are obtained of a black powder which conforms to the compound of the formula (131). The dye obtained dyes natural and synthetic polyamide fibre material in blue shades.

EXAMPLES 32 to 36

Example 31 is repeated, except that the 3.2 parts of 2-amino-5-(benzothiazol-2'-yl)-3-carbethoxythiophene are replaced by an equimolar amount of the amines indicated in column 2 of Table 2 and the 3.65 parts of the coupling component of the formula (105) are or are not replaced by an equimolar amount of a coupling component of the formula (107), affording the azo dyes indicated in the form of the free acids in column 3 which dye natural and synthetic polyamide fibre material in the hues indicated in column 4.

TABLE 2

| Ex. | Amine | Azo dye | Hue on nylon and wool |
|---|---|---|---|
| 32 | (thiazole-fused benzothiazole with COOCH$_3$ and NH$_2$) | (132) | Blue |
| 33 | (thiazole-fused benzoxazole with COOCH$_2$CH$_3$ and NH$_2$) | (133) | Blue |
| 34 | (thiazole-fused benzoxazole with COOCH$_3$ and NH$_2$) | (134) | Blue |
| 35 | (thiazole-fused benzoxazole with COOCH$_2$CH$_3$ and NH$_2$) | (135) | Blue |

TABLE 2-continued
| Ex. | Amine | Azo dye | Hue on nylon and wool |
|---|---|---|---|
| 36 |  |  (136) | Blue |

EXAMPLE 37

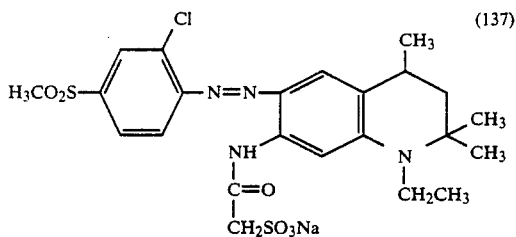

(137)

40 parts of 80% acetic acid and 4 parts of 32% hydrochloric acid are introduced as initial charge at about 10° with stirring. 2.1 parts of 4-amino-3-chlorophenyl methyl sulfone are then added, and the temperature is reduced to 0°. A solution of 0.74 part of $NaNO_2$ in 3 parts of water is then added in the course of 1 minute, the diazotization is carried out at 0° to 3°, and the diazotization mixture is subsequently stirred at 0° to 3° for 45 minutes. 1 part of sulfamic acid is then added, the mixture is briefly stirred, and thereafter 3.65 parts of the coupling component of the formula (105) are added in the course of 1 minute. The mixture is subsequently stirred at 0° to 3° for 30 minutes and thereafter 15 parts of sodium acetate $\times 3H_2O$ are added in 3 portions over 15 minutes. After a further 30 minutes' stirring at 0° to 3° a solution of 6 parts of sodium acetate, 3 parts of sodium carbonate and 30 parts of water is added in the course of 30 minutes during which the reaction mixture warms to not more than 20°. 100 parts of a 15% aqueous sodium chloride solution are then added in the course of 10 minutes, and the dye obtained is filtered off and dried at 50° in vacuo. 6 parts are obtained of a reddish powder which conforms to a compound of the formula (137). The dye obtained dyes natural and synthetic polyamide fibre material in red shades.

EXAMPLES 38 TO 65

Example 37 is repeated, except that the 2.1 parts of 4-amino-3-chlorophenyl methyl sulfone are replaced by an equimolar amount of the amines indicated in column 2 of Table 3 and the 3.65 parts of the coupling component of the formula (105) are or are not replaced by an equimolar amount of a coupling component of the formula (107), affording the azo dyes indicated in the form of the free acids in column 3 which dye natural and synthetic polyamide fibre material in the hues indicated in column 4.

TABLE 3

| Ex. | Amine | Azo dye | Hue on nylon and wool |
|---|---|---|---|
| 38 | (structure with phenyl-SO₂-phenyl-NH₂) | (138) | Yellowish red |
| 39 | (structure with cyclohexyl-CH₃-N-SO₂-phenyl-NH₂) | (139) | Yellowish red |
| 40 | (structure with 4-chlorophenyl-SO₂-phenyl(SO₂CO₂CH₃)-NH₂) | (140) | Red |

TABLE 3-continued
| Ex. | Amine | Azo dye | Hue on nylon and wool |
|---|---|---|---|
| 41 |  |  (141) | Red |
| 42 | 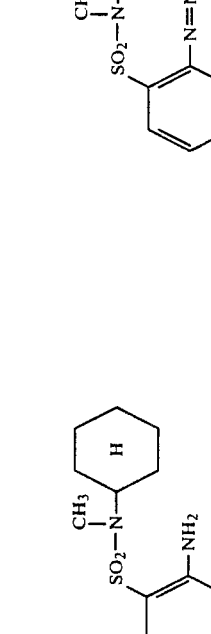 |  (142) | Yellowish red |
| 43 |  |  (143) | Yellowish red |

TABLE 3-continued
| Ex. | Amine | Azo dye | Hue on nylon and wool |
|---|---|---|---|
| 44 | 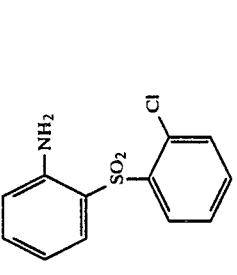 | 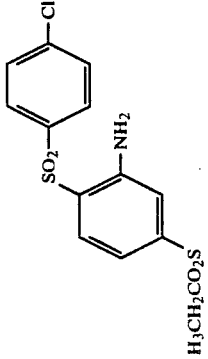 (144) | Red |
| 45 | 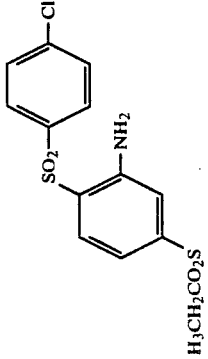 | 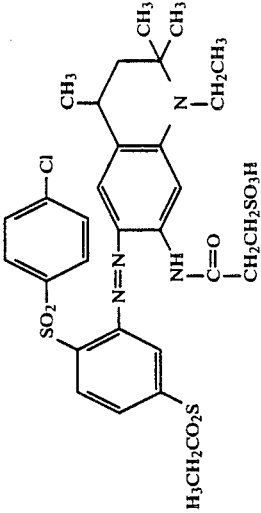 (145) | Red |
| 46 | 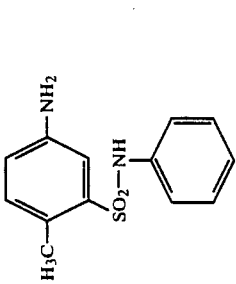 | 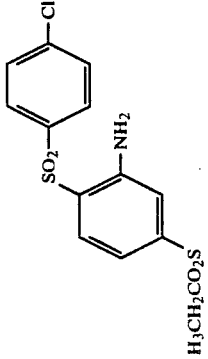 (146) | Orange |

TABLE 3-continued

| Ex. | Amine | Azo dye | Hue on nylon and wool |
|---|---|---|---|
| 47 | 4-aminobenzenesulfonamide (H₂NO₂S-C₆H₄-NH₂) | (147) | Scarlet |
| 48 | 4-aminobenzenesulfonamide (H₂NO₂S-C₆H₄-NH₂) | (148) | Scarlet |
| 49 | 2-amino-4-chloro-1-(2-chlorophenoxy)benzene | (149) | Scarlet |

TABLE 3-continued
| Ex. | Amine | Azo dye | Hue on nylon and wool |
|---|---|---|---|
| 50 |  | 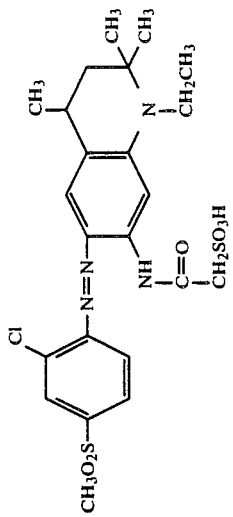 (150) | Scarlet |
| 51 | 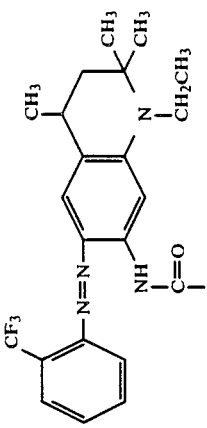 | (151) | Red |
| 52 | 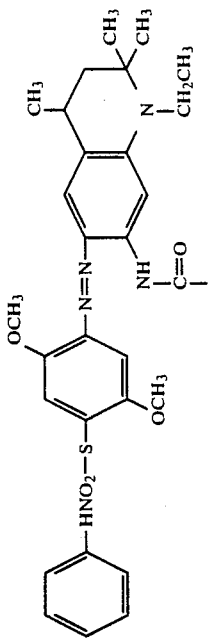 | (152) | Orange |
| 53 | 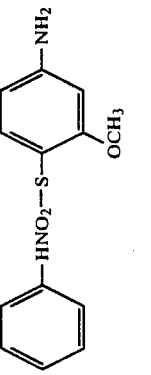 | (153) | Red |

TABLE 3-continued

| Ex. | Amine | Azo dye | Hue on nylon and wool |
|---|---|---|---|
| 54 | H₃CO₂S–C₆H₄–NH₂ | (154) | Red |
| 55 | H₃CO₂S–C₆H₄–NH₂ | (155) | Red |
| 56 | 2-SO₂CH₃–C₆H₄–NH₂ | (156) | Red |
| 57 | 2-SO₂CH₃–C₆H₄–NH₂ | (157) | Red |

TABLE 3-continued

| Ex. | Amine | Azo dye | Hue on nylon and wool |
|---|---|---|---|
| 58 | (structure with naphthalene-SO₂-, SO₂NH₂, NH₂, SO₃H) | (158) | Red |
| 59 | (structure with tolyl-SO₂-, naphthalene-SO₃H, NH₂, SO₂NH-) | (159) | Red |
| 60 | (structure with tolyl-SO₂-, phenyl-SO₃H, NH₂, SO₂NH-) | (160) | Red |

TABLE 3-continued

| Ex. | Amine | Azo dye | Hue on nylon and wool |
|---|---|---|---|
| 61 | (structure) | (161) | Red |
| 62 | (structure) | (162) | Bluish red |
| 63 | (structure) | (163) | Bluish red |

TABLE 3-continued

| Ex. | Amine | Azo dye | Hue on nylon and wool |
|---|---|---|---|
| 64 | ![structure: 4-methylphenyl-SO2-S-phenyl with NH2 and SO3H substituents] | ![azo dye structure (164)] | Bluish red |
| 65 | ![structure: hexamethyleneimine-N-SO2-phenyl-NH2] | ![azo dye structure (165)] | Red |

The procedure of Examples 37 to 65 is followed, except that the coupling component of the formula (105) or (107) is replaced by a coupling component of the formula (106) or (108). This produces analogous dyes which dye synthetic and natural polyamide material in the indicated shades.

EXAMPLE 66

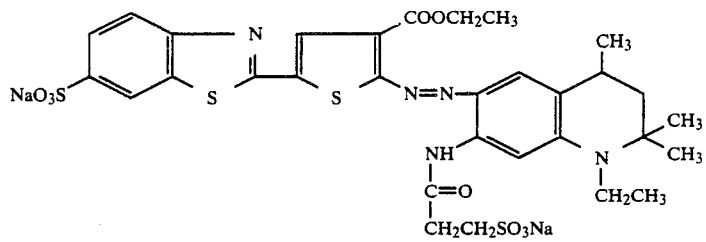

22.5 parts of 100% acetic acid, 33 parts of 80% acetic acid and 12 parts of 32% hydrochloric acid are introduced as the initial charge at about 10° with stirring. Thereafter 4.27 parts of 2-amino-5-(2'-benzothiazolyl-6'-sulfonic acid)-3-ethoxycarbonylthiophene are added in the course of about a minute, and the temperature is reduced to 0°. Thereafter a solution of 0.74 part of sodium nitrite and 3 parts of water is added dropwise at 0° to 2° in the course of about 3 minutes. The mixture is subsequently stirred at 0° to 2° for 25 minutes, 1 part of sulfamic acid is added, and the mixture is briefly stirred again. Thereafter 3.76 parts of N-ethyl-7-β-sulfopropionylamido-2,2,4-trimethylquinoline are sprinkled in over about 1 minute, and the reaction mixture is subsequently stirred for about 10 minutes. 24 parts of sodium acetate×3 H₂O are then added in 4 portions over 30 minutes, and the mixture is subsequently stirred at 0° to 2° for 1 hour. Thereafter a solution of 6 parts of sodium acetate×3 H₂O, 3 parts of sodium carbonate and 30 parts of water is then added dropwise, followed by 125 parts of an approximately 25% aqueous sodium chloride solution, and the dye is filtered off and dried at 50° in vacuo. 8.9 parts are obtained of a powder which conforms to a compound of the formula (166). The dye obtained dyes synthetic polyamide material in blue shades.

EXAMPLES 67 TO 82

Example 66 is repeated, except that the 4.27 parts of 2-amino-5-(2'-benzothiazolyl-6'-sulfonic acid)-3-ethoxycarbonylthiophene are replaced by an equimolar amount of one of the amines indicated in Table 4 below of the formula

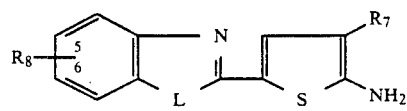

(166)

where L, $R_7$ and $R_8$ are each as defined in columns 2, 3 and 4 of Table 4 below and the 3.76 parts of N-ethyl-7-β-sulfopropionylamido-2,2,4-trimethylquinoline are replaced by an equimolar amount of one of the coupling components indicated in Table 4 of the formula

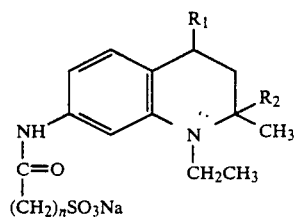

where $R_1$, $R_2$ and n are each as defined in columns 5, 6 and 7 of Table 4. This produces azo dyes which dye synthetic polyamide in the hues indicated in column 8.

TABLE 4

| Ex. | L | $R_7$ | $R_8$ | $R_1$ | $R_2$ | n | Hue on nylon and wool |
|---|---|---|---|---|---|---|---|
| 67 | —S— | —COOCH₂CH₃ | 6-SO₃Na | —CH₃ | —CH₃ | 1 | blue |
| 68 | —S— | —CONH₂ | 6-SO₃Na | —CH₃ | —CH₃ | 1 | blue |
| 69 | —O— | —CONH₂ | 5-SO₃Na | —CH₃ | —CH₃ | 1 | blue |
| 70 | —O— | —CONH₂ | 6-SO₃Na | —CH₃ | —CH₃ | 1 | blue |
| 71 | —S— | —CONH₂ | 5-SO₃Na | —H | —H | 1 | blue |
| 72 | —S— | —CONH₂ | 6-SO₃Na | —H | —H | 1 | blue |
| 73 | —O— | —CONH₂ | 5-SO₃Na | —H | —H | 1 | blue |
| 74 | —O— | —CONH₂ | 6-SO₃Na | —H | —H | 1 | blue |
| 75 | —S— | —CONH₂ | 6-SO₃Na | —CH₃ | —CH₃ | 2 | blue |
| 76 | —O— | —CONH₂ | 5-SO₃Na | —CH₃ | —CH₃ | 2 | blue |
| 77 | —O— | —CONH₂ | 6-SO₃Na | —CH₃ | —CH₃ | 2 | blue |
| 78 | —S— | —COOCH₂CH₃ | 5-SO₃Na | —CH₃ | —CH₃ | 2 | blue |
| 79 | —S— | —COOCH₂CH₃ | 6-SO₃Na | —H | —H | 2 | blue |
| 80 | —O— | —COOCH₂CH₃ | 5-SO₃Na | —H | —H | 2 | blue |
| 81 | —O— | —COOCH₂CH₃ | 6-SO₃Na | —H | —H | 2 | blue |
| 82 | —S— | —COOCH₂CH₃ | 6-SO₃Na | —H | —H | 1 | blue |

DYEING METHOD I 10 parts of nylon-6.6 fabric are dyed in 500 parts of an aqueous liquor which contains per liter 2 g of ammonium acetate and is adjusted to pH 5 with acetic acid. The amount of dye of Example 9 is 0.7% on weight of fibre. The dyeing time at 98° is 30 to 90 minutes. The dyed nylon-6.6 fabric is then removed and as usual washed and dried.

The result obtained is a blue dyeing on the nylon-6.6 fabric in a pure hue which has good all round fastness properties.

DYEING METHOD II 10 parts of nylon-6.6 fabric are dyed in 500 parts of an aqueous liquor which contains per liter 1 g of monosodium phosphate and is adjusted to pH 6 with disodium phosphate. The amount of dye of Example 31 is 1% on weight of fibre. The dyeing time at 98° is 30 to 90 minutes. The dyed nylon-6.6 fabric is then removed and as usual washed and dried.

The result obtained is a blue dyeing on the nylon-6.6 fabric in a pure hue which has good all round fastness properties.

DYEING METHOD III 10 parts of a wool piece material are dyed in 500 parts of an aqueous liquor. On weight of fibre, the proportion of dye of Example 31 is 0.45%, the proportion of calcined Glauber salt is 5% and the proportion of 80% acetic acid is 2%. The dyeing time at 98° is 30–60 minutes. The blue dye on the conventionally washed and dried piece of wool material has very good all round fastness properties.

What is claimed is:

1. An azo dye of the formula $$D-N=N-\underset{\underset{(CH_2)_nSO_3H}{\overset{NH}{\underset{C=O}{|}}}}{\overset{R_1}{\underset{N}{\bigcirc}}}\overset{R_2,}{\underset{R_4}{R_3}} \quad (1)$$

wherein D is thiazolyl, isothiazolyl, 1,2,4-thiadiazolyl, 1,3,4-thiadiazolyl, benzothiazolyl, benzisothiazolyl, benzoxazolyl, pyrazolyl, imidazolyl, 1,2,3-triazolyl, 1,2,4-triazolyl, thiophenyl, benzothiophenyl, tetrahydrobenzothiophenyl, 7-oxotetrahydrobenzothiophenyl, pyridinyl, indazolyl, phenyl or naphthyl, each of which is unsubstituted or substituted by $C_1$–$C_8$alkyl, $C_1$–$C_8$alkoxy, $C_2$–$C_8$alkanoylamino, $C_2$–$C_8$alkoxycarbonylamino, $C_2$–$C_8$alkanoyl, $C_5$–$C_7$cycloalkylcarbonyl, $C_5$–$C_7$cycloalkylcarbonyl which is substituted in the cycloalkyl ring by $C_1$–$C_4$alkyl, halogen, sulfo or sulfato, benzoyl, benzoyl which is substituted in the phenyl ring by $C_1$–$C_4$alkyl, halogen, sulfo or sulfato, $C_1$–$C_8$alkylthio, sulfo-substituted $C_1$–$C_8$alkylthio, benzothiazole, benzoxazole, $C_1$–$C_4$alkyl-, halogen-, sulfo- or sulfato-substituted benzothiazole or benzoxazole, benzoylamino, amino, mono- or dialkylamino having 1 to 8 carbon atoms in the alkyl moiety, phenylamino, $C_2$–$C_8$alkoxycarbonyl, nitro, cyano, trifluoromethyl, halogen, 1-azacycloheptane-N-sulfonyl, sulfamoyl, sulfamoyl which is monosubstituted or disubstituted on the nitrogen atom by $C_1$–$C_4$alkyl, $C_5$–$C_7$cycloalkyl, phenyl or naphthyl, phenyl- or naphthyl-aminosulfonyl which is substituted in the phenyl or naphthyl ring by $C_1$–$C_4$alkyl, halogen, sulfo or sulfato, phenoxy, phenoxysulfonyl, $C_1$–$C_4$alkyl-, halogen-, sulfo- or sulfato-substituted phenoxy or phenoxysulfonyl, carbamoyl, ureido, hydroxyl, $C_1$–$C_8$alkylsulfonyl, phenylsulfonyl, naphthylsulfonyl, phenyl- or naphthyl-sulfonyl which is substituted in the phenyl or naphthyl ring by $C_1$–$C_4$alkyl, halogen, sulfo or sulfato, carboxyl, sulfomethyl, sulfo, sulfato, thiosulfato, phenylazo or naphthylazo, $R_1$, $R_2$, $R_3$ and $R_4$ are each independently of the others hydrogen or $C_1$–$C_8$alkyl which is unsubstituted or substituted by hydroxyl, $C_1$–$C_4$alkoxy, sulfo, sulfato, thiosulfato, cyano, halogen or phenyl which is unsubstituted or substituted by hydroxyl, $C_1$–$C_4$alkoxy, sulfo, sulfato, thiosulfato, cyano or halogen and n is 1,2,3,4 or 5.

2. An azo dye according to claim 1, wherein D is thiazolyl, isothiazolyl, 1,2,4-thiadiazolyl, 1,3,4-thiadiazolyl, benzothiazolyl, benzisothiazolyl, benzoxazolyl, pyrazolyl, imidazolyl, 1,2,3-triazolyl, 1,2,4-triazolyl, thiophenyl, benzothiophenyl, tetrahydrobenzothiophenyl, 7-oxotetrahydrobenzo[b]thiophenyl, pyridinyl, indazolyl, phenyl or naphthyl, each of which is unsubstituted or substituted by $C_1$–$C_8$alkyl, $C_1$–$C_8$alkoxy, $C_2$–$C_8$alkanoylamino, $C_2$–$C_8$alkoxycarbonylamino, $C_2$–$C_8$alkanoyl, $C_5$–$C_7$cycloalkylcarbonyl, $C_5$–$C_7$cycloalkylcarbonyl which is substituted in the cycloalkyl ring by $C_1$–$C_4$alkyl, halogen, sulfo or sulfato, benzoyl, benzoyl which is substituted in the phenyl ring by $C_1$–$C_4$alkyl, halogen, sulfo or sulfato, benzothiazole, benzoxazole, $C_1$–$C_4$alkyl-, halogen-, sulfo- or sulfato-substituted benzothiazole or benzoxazole, benzoylamino, amino, mono- or dialkylamino having 1 to 8 carbon atoms in the alkyl moiety, phenylamino, $C_2$–$C_8$alkoxycarbonyl, nitro, cyano, trifluoromethyl, halogen, sulfamoyl, sulfamoyl which is monosubstituted or disubstituted on the nitrogen atom by $C_1$–$C_4$alkyl, $C_5$–$C_7$cycloalkyl or phenyl, carbamoyl, ureido, hydroxyl, $C_1$–$C_8$alkylsulfonyl, phenylsulfonyl, phenylsulfonyl which is substituted in the phenyl ring by $C_1$–$C_4$alkyl, halogen, sulfo or sulfato, carboxyl, sulfomethyl, sulfo, sulfato, thiosulfato, phenylazo or naphthylazo.

3. An azo dye according to claim 1, wherein D is thiophenyl, benzothiophenyl, benzisothiazolyl, 1,3,4-thiadiazolyl, 7-oxotetrahydrobenzo[b]thiophenyl or phenyl, each of which is unsubstituted or substituted by $C_1$–$C_8$alkyl, $C_1$–$C_8$alkoxy, $C_2$–$C_8$alkanoyl, carbamoyl, $C_2$–$C_8$alkoxycarbonyl, $C_5$–$C_7$cycloalkylcarbonyl, benzoyl, benzoyl which is substituted in the phenyl ring by $C_1$–$C_4$alkyl, halogen, sulfo or sulfato, $C_1$–$C_8$alkylthio, sulfo-substituted $C_1$–$C_8$alkylthio, benzothiazole, benzoxazole, $C_1$–$C_4$alkyl-, halogen-, sulfo- or sulfato-substituted benzothiazole or benzoxazole, halogen, sulfo, trifluoromethyl, phenylsulfonyl, naphthylsulfonyl, phenyl- or naphthyl-sulfonyl which is substituted in the phenyl or naphthyl ring by $C_1$–$C_4$alkyl, halogen, sulfo or sulfato, $C_1$–$C_8$alkylsulfonyl, 1-azacycloheptane-N-sulfonyl, sulfamoyl, sulfamoyl which is monosubstituted or disubstituted on the nitrogen atom by $C_1$–$C_4$alkyl, $C_5$–$C_7$cycloalkyl, phenyl or naphthyl, phenyl- or naphthyl-aminosulfonyl which is substituted in the phenyl or naphthyl ring by $C_1$–$C_4$alkyl, halogen, sulfo or sulfato, phenoxy, phenoxysulfonyl, $C_1$–$C_4$alkyl-, halogen-, sulfo- or sulfato-substituted phenoxy or phenoxysulfonyl.

4. An azo dye according to claim 1, wherein D is thiophenyl, 7-oxotetrahydrobenzo[b]thiophenyl or phenyl, which is unsubstituted or substituted by $C_1$–$C_8$alkyl, $C_2$–$C_8$alkanoyl, $C_2$–$C_8$alkoxycarbonyl, $C_5$–$C_7$cycloalkylcarbonyl, benzoyl, benzoyl which is substituted in the phenyl ring by $C_1$–$C_4$alkyl, halogen, sulfo or sulfato, benzothiazole, benzoxazole, $C_1$–$C_4$alkyl-, halogen-, sulfo- or sulfato-substituted benzothiazole or benzoxazole, halogen, phenylsulfonyl, phenylsulfonyl which is substituted in the phenyl ring by $C_1$–$C_4$alkyl, halogen, sulfo or sulfato, $C_1$–$C_8$alkylsulfonyl, sulfamoyl which is monosubstituted or disubstituted on the nitrogen atom by $C_1$-$C_4$alkyl, $C_5$-$C_7$cycloalkyl or phenyl.

5. An azo dye according to claim 1, wherein $R_1$ is hydrogen or $C_1$-$C_4$alkyl.

6. An azo dye of claim 5 wherein $R_1$ is methyl.

7. An azo dye according to claim 1, wherein $R_2$ and $R_3$ are each independently of the other hydrogen or $C_1$-$C_4$alkyl.

8. An azo dye of claim 7 wherein $R_2$ and $R_3$ are methyl.

9. An azo dye according to claim 1, wherein $R_4$ is $C_1$-$C_4$alkyl, or benzyl.

10. An azo dye of claim 9 wherein $R_4$ is ethyl.

11. An azo dye according to claim 1, wherein n is 1, 2 or 3.

12. An azo dye of claim 11 wherein n is 1 or 2.

13. An azo dye according to claim 1, wherein $R_1$ is hydrogen or $C_1$-$C_4$alkyl, $R_2$ and $R_3$ are each independently of the other hydrogen or $C_1$-$C_4$alkyl, $R_4$ is $C_1$-$C_4$alkyl, and n is 1 or 2.

14. An azo dye of claim 13 wherein $R_1$, $R_2$ and $R_3$ are methyl, $R_4$ is ethyl and n is 1 or 2.

15. An azo dye according to claim 1 of the formula

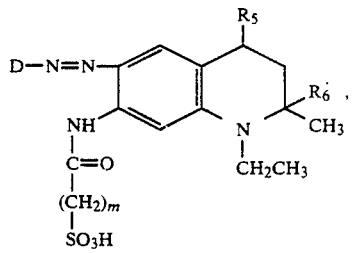

(4)

where $R_5$ and $R_6$ are each independently of the other hydrogen or methyl and m is 1 or 2.

16. An azo dye according to claim 15, wherein $R_5$ and $R_6$ are both hydrogen or methyl.

17. An azo dye according to claim 1, which contains only two sulfo groups.

* * * * *